(12) United States Patent
Stuart et al.

(10) Patent No.: US 11,571,245 B2
(45) Date of Patent: Feb. 7, 2023

(54) BONE STABILIZING IMPLANTS AND METHODS OF PLACEMENT ACROSS SI JOINTS

(71) Applicant: SI-Bone Inc., Santa Clara, CA (US)

(72) Inventors: Mary E. Stuart, Santa Clara, CA (US); Bret W. Schneider, San Jose, CA (US); Francois Follini, Austin, TX (US); Craig S. Bartlett, Shelburne, VT (US); Bharat M. Desai, Golden, CO (US); Michael J. Gardner, Menlo Park, CA (US); GianLuigi Moro, Rodano (IT); Sven H. Van Helden, Hattem (NL); Kyle L. Nishkian, San Francisco, CA (US); David W. Polly, Edina, MN (US); Jed S. Vanichkachorn, Richmond, VA (US); Andy J. Kranenburg, Central Point, OR (US); Sharad S. Rajpal, Golden, CO (US); Nikolai G. Rainov, Augsburg (DE)

(73) Assignee: SI-Bone Inc., Santa Clara, CA (US)

( * ) Notice: Subject to any disclaimer, the term of this patent is extended or adjusted under 35 U.S.C. 154(b) by 0 days.

(21) Appl. No.: 17/664,353

(22) Filed: May 20, 2022

(65) Prior Publication Data
US 2022/0273446 A1    Sep. 1, 2022

Related U.S. Application Data

(63) Continuation of application No. PCT/US2020/062275, filed on Nov. 25, 2020.
(Continued)

(51) Int. Cl.
*A61B 17/70*     (2006.01)
*B33Y 80/00*    (2015.01)
(Continued)

(52) U.S. Cl.
CPC ........ *A61B 17/7055* (2013.01); *A61B 17/864* (2013.01); *A61F 2/30988* (2013.01);
(Continued)

(58) Field of Classification Search
CPC ..... A61B 17/7055; A61B 17/84; A61B 17/86; A61B 17/864; A61B 17/869;
(Continued)

(56) References Cited

U.S. PATENT DOCUMENTS

| | | |
|---|---|---|
| 1,951,278 A | 3/1934 | Ericsson |
| 2,136,471 A | 11/1938 | Schneider |

(Continued)

FOREIGN PATENT DOCUMENTS

| | | |
|---|---|---|
| CN | 1123944 A | 8/1996 |
| CN | 1190882 A | 8/1998 |

(Continued)

OTHER PUBLICATIONS

Acumed; Acutrak Headless Compressioin Screw (product information); 12 pgs; © 2005; retrieved Sep. 25, 2014 from http://www.rcsed.ac.uk/fellows/lvanrensburg/classification/surgtech/acumed/manuals/acutrak-brochure%200311.pdf.
(Continued)

*Primary Examiner* — Eduardo C Robert
*Assistant Examiner* — Christina Negrellirodriguez
(74) *Attorney, Agent, or Firm* — Shay Glenn LLP

(57) ABSTRACT

Threaded sacro-iliac joint stabilization (e.g., fusion, fixation) implants and methods of implantation and manufacture. Some implants include a threaded distal region, an optionally threaded central region, and an optionally threaded proximal region. The distal, central, and proximal regions have lengths such that when the implant is laterally implanted across a SI joint, the distal region can be positioned in a sacrum, the central region can be positioned
(Continued)

across an SI-joint, and the proximal region can be positioned in an ilium.

12 Claims, 12 Drawing Sheets

Related U.S. Application Data

(60) Provisional application No. 62/941,507, filed on Nov. 27, 2019.

(51) Int. Cl.
  *A61B 17/86* (2006.01)
  *A61F 2/30* (2006.01)
(52) U.S. Cl.
  CPC ..... *B33Y 80/00* (2014.12); *A61F 2002/30622* (2013.01); *A61F 2002/30784* (2013.01); *A61F 2002/30858* (2013.01); *A61F 2002/30985* (2013.01); *A61F 2002/30995* (2013.01)
(58) Field of Classification Search
  CPC ..... A61B 17/8625; A61B 17/863; F16B 5/02; F16B 5/025; F16B 25/0005; F16B 25/0036; F16B 25/0042; F16B 25/0052; F16B 25/0057; F16B 25/0068
  USPC ......... 606/246, 300, 301, 304, 309, 311–317
  See application file for complete search history.

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |

(56) References Cited

U.S. PATENT DOCUMENTS

| | | |
|---|---|---|
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,920,477 B2 | 12/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,348 B2 | 4/2016 | Emstad |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| 9,615,856 B2 | 4/2017 | Arnett et al. |
| 9,622,783 B2 | 4/2017 | Reiley et al. |

(56) References Cited

U.S. PATENT DOCUMENTS

| | | |
|---|---|---|
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,820,789 B2 | 11/2017 | Reiley |
| 9,839,448 B2 | 12/2017 | Reckling et al. |
| 9,848,892 B2 | 12/2017 | Biedermann et al. |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| 9,956,013 B2 | 5/2018 | Reiley et al. |
| 9,993,276 B2 | 6/2018 | Russell |
| 10,004,547 B2 | 6/2018 | Reiley |
| 10,058,430 B2 | 8/2018 | Donner et al. |
| 10,166,033 B2 | 1/2019 | Reiley et al. |
| 10,188,442 B2 | 1/2019 | Mazel |
| 10,194,962 B2 | 2/2019 | Schneider et al. |
| 10,201,427 B2 | 2/2019 | Mauldin et al. |
| 10,219,885 B2 | 3/2019 | Mamo et al. |
| 10,258,380 B2 | 4/2019 | Sinha |
| 10,271,882 B2 | 4/2019 | Biedermann et al. |
| 10,335,217 B2 | 7/2019 | Lindner |
| 10,363,140 B2 | 7/2019 | Mauldin et al. |
| 10,426,533 B2 | 10/2019 | Mauldin et al. |
| 10,492,921 B2 | 12/2019 | McShane, III et al. |
| 10,531,904 B2 | 1/2020 | Kolb |
| 10,653,454 B2 | 5/2020 | Frey et al. |
| 10,667,923 B2 | 6/2020 | Sullivan et al. |
| 10,729,475 B2 | 8/2020 | Childs |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,799,367 B2 | 10/2020 | Vrionis et al. |
| 10,806,597 B2 | 10/2020 | Sournac et al. |
| 10,842,634 B2 | 11/2020 | Pasini et al. |
| 10,856,922 B2 | 12/2020 | Loke et al. |
| 10,932,838 B2 | 3/2021 | Mehl et al. |
| 10,940,008 B2 | 3/2021 | Patel |
| 10,959,758 B2 | 3/2021 | Mesiwala et al. |
| 10,993,754 B2 | 5/2021 | Kuntz et al. |
| 11,071,573 B2 | 7/2021 | Schneider et al. |
| 11,116,519 B2 | 9/2021 | Sand et al. |
| 11,147,688 B2 | 10/2021 | Reckling et al. |
| 11,234,830 B2 | 2/2022 | Mesiwala et al. |
| 11,291,485 B2 | 4/2022 | Mauldin et al. |
| 11,337,821 B2 | 5/2022 | Mauldin et al. |
| 11,369,419 B2 | 6/2022 | Mesiwala et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |

(56) References Cited

U.S. PATENT DOCUMENTS

| | | |
|---|---|---|
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |

(56) References Cited

U.S. PATENT DOCUMENTS

| | | |
|---|---|---|
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0272646 A1* | 10/2015 | Russell .............. A61B 17/8841 606/93 |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0157908 A1 | 6/2016 | Cawley et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2018/0104063 A1 | 4/2018 | Asaad |
| 2018/0104068 A1 | 4/2018 | Sack |
| 2018/0110624 A1 | 4/2018 | Arnone |
| 2018/0110626 A1 | 4/2018 | McShane, III et al. |
| 2018/0200063 A1 | 7/2018 | Kahmer et al. |
| 2018/0214192 A1 | 8/2018 | Roby et al. |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0243097 A1 | 8/2018 | Jones et al. |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0296363 A1 | 10/2018 | Berry |
| 2018/0303623 A1 | 10/2018 | Shoshtaev |
| 2018/0303624 A1 | 10/2018 | Shoshtaev |
| 2018/0317971 A1 | 11/2018 | Prevost |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0091027 A1 | 3/2019 | Asaad et al. |
| 2019/0125408 A1 | 5/2019 | Asfora et al. |

(56) References Cited

U.S. PATENT DOCUMENTS

| | | |
|---|---|---|
| 2019/0133613 A1 | 5/2019 | Reiley et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1 | 10/2019 | Lindsey et al. |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |
| 2019/0343641 A1 | 11/2019 | Mauldin et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388242 A1 | 12/2019 | Harris et al. |
| 2020/0000595 A1 | 1/2020 | Jones et al. |
| 2020/0008817 A1 | 1/2020 | Reiley et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0093603 A1 | 3/2020 | Manwill et al. |
| 2020/0100822 A1 | 4/2020 | Lipow |
| 2020/0129214 A1 | 4/2020 | Pepper et al. |
| 2020/0138485 A1 | 5/2020 | Kuwamura et al. |
| 2020/0138492 A1 | 5/2020 | Kavanagh |
| 2020/0170679 A1 | 6/2020 | Sciubba et al. |
| 2020/0246158 A1 | 8/2020 | Bergey |
| 2020/0268518 A1 | 8/2020 | Suh et al. |
| 2020/0323563 A1 | 10/2020 | Rezach et al. |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0107093 A1 | 4/2021 | Tempco |
| 2021/0153911 A1 | 5/2021 | Stuart et al. |
| 2021/0169660 A1 | 6/2021 | Reckling et al. |
| 2021/0212734 A1 | 7/2021 | Mesiwala et al. |
| 2021/0212833 A1 | 7/2021 | Chin et al. |
| 2022/0031474 A1 | 2/2022 | Reckling et al. |
| 2022/0096098 A1 | 3/2022 | Sand et al. |
| 2022/0117640 A1 | 4/2022 | Schneider et al. |
| 2022/0151668 A1 | 5/2022 | Mauldin et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3484387 A1 | 5/2019 |
| EP | 3593745 A2 | 1/2020 |
| EP | 3616634 A1 | 3/2020 |
| EP | 3661441 A1 | 6/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015510506 A | 4/2015 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2013/000071 A1 | 1/2013 |
| WO | WO2013/119907 A1 | 8/2013 |
| WO | WO2017/147537 A1 | 8/2017 |
| WO | WO2020/168269 A1 | 8/2020 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Mesiwala et al.; U.S. Appl. No. 17/649,265 entitled "Implants for spinal fixation and or fusion," filed Jan. 28, 2022.

Mesiwala et al.; U.S. Appl. No. 17/649,296 entitled "Implants for spinal fixation and or fusion," filed Jan. 28, 2022.

Mauldin et al.; U.S. Appl. No. 17/650,473 entitled "Fenestrated implant," filed Feb. 9, 2022.

Follini et al.; U.S. Appl. No. 17/777,679 entitled "Rod coupling assemblies for bone stabilization constructs," filed May 18, 2022.

Mauldin et al.; U.S. Appl. No. 17/664,582 entitled "Integrated implant," filed May 23, 2022.

(56) References Cited

OTHER PUBLICATIONS

Stuart et al.; U.S. Appl. No. 17/812,945 entitled "Sacro-iliac joint stabilizing implants and methods of implantation," filed Jul. 15, 2022.

* cited by examiner

1044

BONE STABILIZING IMPLANTS AND METHODS OF PLACEMENT ACROSS SI JOINTS

CROSS REFERENCE TO RELATED APPLICATIONS

This application is a continuation application of International Application No. PCT/US2020/062275, filed Nov. 25, 2020, which claims the benefit of priority to U.S. Provisional Application No. 62/941,507, filed Nov. 27, 2019, the entire disclosure of which are incorporated by reference herein in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The SI-Joint functions in the transmission of forces from the spine to the lower extremities, and vice-versa. The SI-Joint has been described as a pain generator for up to 22% of lower back pain. To relieve pain generated from the SI Joint, SI Joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. There is a continued need for improved threaded SI Joint fixation and fusion implants.

SUMMARY OF THE DISCLOSURE

One aspect of the disclosure is a threaded bone implant ("implant"). The implant may include an elongate body having a distal end and a proximal end. The elongate body may include a threaded multi-lead distal region, a threaded single-lead central region disposed proximally of the multi-lead distal region, and a threaded multi-lead proximal region disposed proximally of the single-lead central region. The elongate body has a length, and the threaded multi-lead distal region, the threaded single-lead central region, and the threaded multi-lead proximal region may each have individual lengths such that when the implant is laterally implanted, the multi-threaded distal region can be positioned in a sacrum, the single-lead central region can be positioned across a SI-joint, and the multi-lead proximal region can be positioned in an ilium.

In this aspect, the threaded multi-lead distal region may be better adapted to anchor into dense sacral bone than the threaded single lead central region.

In this aspect, the threaded multi-lead proximal region may be better configured to anchor into dense iliac bone than the threaded single lead central region.

In this aspect, one or both of the multi-lead distal region and the multi-lead proximal region may be a dual-lead threaded region.

In this aspect, the multi-lead distal region, single-lead central region, and multi-lead proximal region may all comprise an inner shank from which the respective thread radially extends and a porous network of interconnected struts disposed about the inner shank and in between threads. A proximal region or portion of the threaded single-lead central region may be free of a porous network of interconnected struts, and a threaded single-lead central region may have a major diameter from 9 mm to 11 mm (the outer diameter of the thread).

In this aspect, a threaded multi-lead distal region may be a dual-lead distal region comprising a pattern of high and low threads.

In this aspect, a threaded multi-lead proximal region may be a dual-lead distal region comprising a pattern of high and low threads.

In this aspect, a first thread may be continuous and extend from the distal region, through the central region, and into the proximal region. A continuous thread in this regard may be interrupted by a plurality of fenestrations and/or flutes extending through the elongate body.

In this aspect, the elongate body may further have a plurality of helical flutes formed therein, each of the plurality of flutes extending in the multi-lead distal region, the single-lead central region, and optionally in the multi-lead proximal region. A plurality of helical flutes may consist of three helical flutes in the elongate implant body. Each of a plurality of flutes may have a plurality of fenestrations aligned with the respective flute, the fenestrations spaced from each other along a length of the flute and extending into an elongate body central lumen or area. Each of a plurality of fenestrations may have a radially inward tapered configuration. At least one of a plurality of fenestrations may be disposed in the distal region, at least one of the plurality of fenestrations may be disposed in the central region, and at least one of the plurality of fenestrations may be disposed in the proximal region. In some embodiments the proximal region is free of fenestrations.

In this aspect, a first fenestration in the distal region may be larger than a second fenestration in the central region, and optionally each of a plurality of distal fenestrations may be larger than each of a plurality of central fenestrations.

In this aspect, the elongate body may further comprise a plurality of fenestrations therethrough. A first fenestration in the distal region may be larger than a second fenestration in the central region. In some embodiments, each of a plurality of distal fenestrations may be larger than each of a plurality of central fenestrations.

In this aspect, a proximal region of the elongate body may be tapered, with a proximal end having a larger radial dimension than a distal end of the proximal region.

In this aspect, at least one of the threads may have an inverse fillet that is curved.

In this aspect, a proximal end of the elongate body may be counter-sunk.

In this aspect, the length of the distal region may be from 10 mm to 22 mm.

In this aspect, the length of the central region may be from 8 mm to 56 mm.

In this aspect, the length of the proximal region may be from 6 mm to 10 mm.

This aspect may further include any suitable implant feature described herein.

One aspect of this disclosure is a threaded bone stabilization implant adapted for a lateral delivery and sized for placement across a sacro-iliac ("SI") joint. The implant includes an elongate body having a distal end and a proximal end. The elongate body may include a threaded distal region, a threaded central region disposed proximally of the distal region, and a proximal region disposed proximally of the central region. The elongate body may further include a plurality of helical flutes, each of the plurality of helical flutes having formed therethrough a plurality of fenestrations extending into a central lumen. The body may have a length, and the threaded distal region, the threaded central region, and the proximal region may each have individual lengths such that when the implant is laterally implanted, the threaded distal region can be positioned in a sacrum, the threaded central region can be positioned across an SI-joint, and the proximal region can be positioned in an ilium.

This aspect may additionally comprise any other suitable threaded implant feature described herein.

One aspect of this disclosure is a threaded bone implant. The implant includes an elongate body extending from a distal end to a proximal end. The elongate body may include one or more helical threads, each of the one or more helical threads extending axially along at least a portion of the elongate body. The elongate body may include an inner shank or inner member from which the one or more helical threads radially extend. The elongate body may also include a porous network of interconnected struts disposed about the inner shank (or inner member) and about a longitudinal axis of the elongate bone implant body. A porous network of interconnected struts may be disposed between the one or more helical threads along at least a section of the elongate body, and optionally disposed in each of a distal region, a central region, and a proximal region of the implant. In some examples a porous network of interconnected struts has a continuous helical configuration through a distal region, a central region, and into a proximal region. Continuous in this context and as used herein includes discontinuities in the porous network due to one or more flutes and/or one or more fenestrations. A porous network of interconnected struts may have an outer dimension that is less than a major diameter of the one or more helical threads.

This aspect may include any other suitable threaded implant feature described herein.

One aspect of this disclosure is a method of manufacturing a threaded bone implant. The method may include printing a threaded bone implant from a distal end to a proximal end (although printing from a proximal end (head) to a distal end (tip) may be used in some alternative embodiments). Printing the implant may include printing an inner shank, printing one or more helical threads extending radially from the inner shank, each of the one or more helical threads extending along at least a portion of the threaded bone implant. The method may include printing a porous network of interconnected struts about the inner shank, about a long axis of the elongate bone implant body, and between at least a section of the one or more helical threads. The porous network of interconnected struts generally has an outer dimension less than a major diameter of the one or more helical threads.

This aspect may include any other suitable method step herein, and may be a computer executable method stored in a memory and adapted to be executed by a processor or processing component, concepts of which are known (e.g., one or more pieces of software, an algorithm, etc.)

One aspect of the disclosure is a method of 3D printing a threaded bone implant. The method may include printing a threaded bone implant from a distal end to a proximal end. Printing the implant may include printing a sacrificial distal tip, printing a threaded bone implant above the sacrificial distal tip, and subsequent in time to printing the threaded bone implant, removing the sacrificial tip and forming a distal end on the threaded bone implant.

This aspect may include any other suitable method described herein.

One aspect of this disclosure is a 3D printed threaded bone implant. The implant may include a 3D printed implant body having a distal end and a proximal end. The implant body may have one or more threads thereon extending radially outward from an inner shank. At least one thread may form an angle greater than 45 degrees relative to a long axis of the implant body.

This aspect may include any other suitable feature related to threaded bone implants herein.

DETAILED DESCRIPTION

The disclosure relates generally to threaded bone stabilizing implants, which may be used for fixation and/or fusion, for example. The bone stabilizing implants described herein are generally sized and configured to be delivered in a lateral delivery pathway and implanted such that a distal region of the implant is implanted in a sacrum, an intermediate region is implanted in or across a sacro-iliac ("SI") joint, and a proximal region is implanted in an ilium. The bone implants herein include one or more threads along at least a portion of the implant, which allows the implants to be rotated into and anchored into bone during implantation. When an implant herein is referred to as a threaded implant, it refers to an implant having one or more threads, any one of which may extend along at least a portion of a length of the implant.

The threaded bone implants herein generally include different regions or portions along their lengths that are sized and/or configured to provide functionality based at least partially on the anatomical region in which they implanted. For example, implants herein may have distal regions that are sized (e.g., length and/or width) and configured (e.g., threaded) such that the distal region is adapted with functionality to anchor into relatively more dense cancellous sacral bone. The functionality may be compared relative to other regions of the implant that are not so sized and/or configured, or to other types of implants that are not so sized and/or configured in the manner(s) described herein.

The disclosure herein may be related to disclosure from U.S. Publication. Nos. 2018/0228621, 2013/0296953 and 20150105828, the entire disclosures of which are incorporated by reference herein for all purposes.

Figure 1:
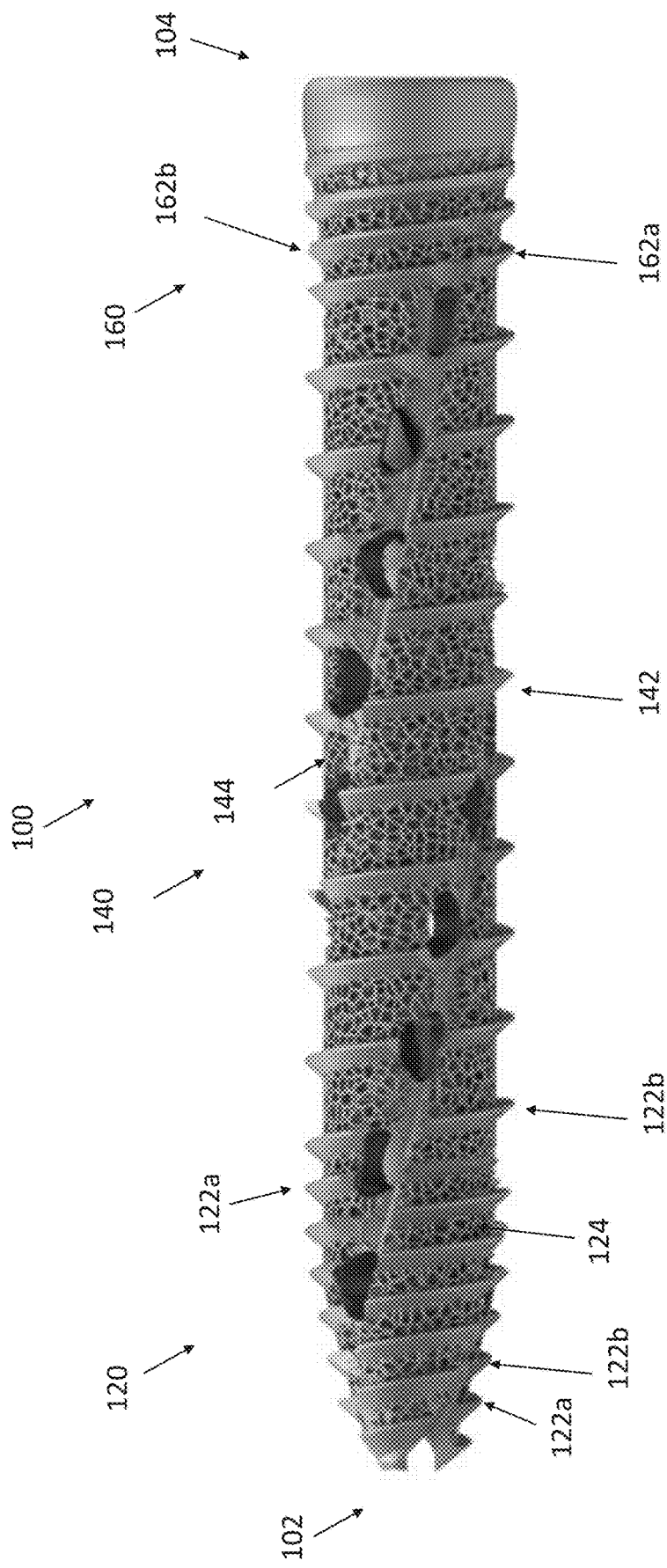
FIG. 1 is a side view of an exemplary threaded implant.

FIG. 1 illustrates an exemplary bone stabilization implant 100 that includes an elongate body as shown, the elongate body extending from distal end 102 to proximal end 104. The elongate body includes distal anchor region 120, intermediate or central region 140, and proximal region 160. In this embodiment, distal region 120 includes a threaded region that is multi-lead, and in this particular example is dual-lead, with threads 122a and 122b shown in FIG. 1.

Distal region 120 also includes a porous network of interconnected struts 124 in between the threads, one region of which is labeled in FIG. 1. A porous network of interconnected struts may be referred to herein as a porous lattice. FIG. 1 illustrates an example of a porous network of interconnected struts that may be considered to have a general helical configuration that extends between helical threads of the threaded region, as shown. The helical configuration of the porous lattice may be interrupted by one or more fenestrations and/or flutes where no lattice is present (such as shown in FIG. 1), but the porous lattice may still be considered to have a general helical configuration in these examples.

Distal region 120 is multi-lead (dual-lead in this example), the configuration of which adapts distal region 120 to more securely anchor into dense cancellous sacral bone.

The porous lattices herein may comprise an outer porous network of interconnected struts, an example of which is shown in FIG. 1, and which are described in more detail below. Any of the individual struts herein may also be referred to as a beam. Generally, the porous regions in between the threads preferably have a smooth outer profile to facilitate rotational insertion and proper anchoring. Alternatively stated, it is generally desirable for the porous regions in between threads to avoid having a significantly rough outer surface with exposed strut ends, which may deleteriously damage the adjacent bone and result in less stable anchoring. The porous network may have an irregular configuration of struts, or it may have a regular pattern of struts, or a combination thereof. It is therefore understood that the term lattice as used herein does not require a regular or repeating pattern of struts. Additional exemplary features of porous networks of interconnected struts are described below.

The implant 100 also includes central or intermediate region 140, which is sized and configured (including relative to other implants regions) to be positioned across a SI joint when the implant 100 is delivered laterally across the SI joint. Central region 140 includes a fewer-lead threaded region than distal region 120 and proximal region 160, and in this embodiment is single-lead. In this embodiment thread 142 in central region 140 is considered to continue into distal region 120 as thread 122b, as shown, but in alternative embodiments the central region thread may be considered part of a different thread that does not continue or extend into distal region 120. Thread 122b is considered continuous with thread 142 from distal region 120 into central region 140, even though the thread is interrupted one or more times by fenestrations and fluted regions, which are described in more detail below.

Central region 140 includes a porous network of interconnected struts 144 (which may be referred to here as a lattice), only one region of which is labeled in FIG. 1. Lattice 144, like lattice 124, is disposed between threads in central region 140. The porous lattice 144 may be considered continuous with porous lattice 124 in that they together approximate a generally helical configuration extending from distal region 120 into central region 140, which again is interrupted by one or more fenestrations and fluted region as shown.

The exemplary single-lead design in central region 140 provides for relatively greater axial spacing between threads, compared to, for example, distal region 120. This relatively greater axially spacing creates a greater porous lattice 144 surface area, which is better adapted and configured to facilitate ingrowth and/or ongrowth when central region 140 is implanted across the SI joint. Distal region 120 and central region 140 are examples of regions in which the central region has a relatively greater spacing between threads, which provides for a greater porous surface area between threads.

The elongate body also includes proximal region 160, which includes a threaded region with a greater lead than central region 140. In this example, proximal region 160 includes a threaded region that is dual-lead, as shown. Thread 162a in proximal region 160 is continuous with thread 142 in central region 140, although in alternative embodiments they may not be continuous. It is again understood that the phrase continuous in this context includes one or more interruptions with fluted region and/or fenestrations, as shown in FIG. 1. The multi-lead threaded region in proximal region 160 facilitates strong anchoring in dense iliac bone when implant 100 is implanted laterally across a SI joint.

As mentioned above, implants herein may have a distal region, a central region and a proximal region that are each configured and sized to provide one or more functions based on the anatomical region in which they are positioned after the implant is fully implanted. In some embodiments, any of the distal regions herein (e.g., distal region 120 in FIG. 1) may have a length from 10 mm to 22 mm, for example. This may ensure that the multi-lead region is anchored into dense sacral bone near the mid sacrum. In some embodiments, any of the central regions herein (e.g., central region 140) may have a length from 8 mm to 56 mm. This may ensure that the central region is positioned across the SI joint, with the relatively larger porous surface area extending across the joint to facilitate one or more of ingrowth and/or ongrowth areas. In some embodiments, any of the proximal regions herein (e.g., proximal region 160 in FIG. 1) may have lengths from 6 mm to 10 mm, which can ensure that the multi-lead threaded proximal region is anchored into dense iliac bone. The proximal regions herein with respect to their lengths are not considered to include a proximal end of the elongate body that is free of threads, such as where reference number 104 is pointing in FIG. 1.

Implant body 100 also includes an inner shank or inner member from which the one or more threads and one or more porous lattice regions radially extend. The inner shank may be considered the same or similar to a shank of a screw or other threaded body. The inner shanks herein need not be considered to be continuous structures, and may include one or more breaks or discontinuities therein, such as one or more fenestrations extending therethrough. The inner shank or inner members herein in this context may be considered to include inner surfaces from which one or more threads and one more porous lattice structures extend radially therefrom.

The distal region 120 is tapered towards its distal end, as shown in FIG. 1, a feature of which may be incorporated into any of the implants herein. Distal end 102 in this example also includes sharpened distal end elements, which may be incorporated into any of the implants herein.

Figure 2:
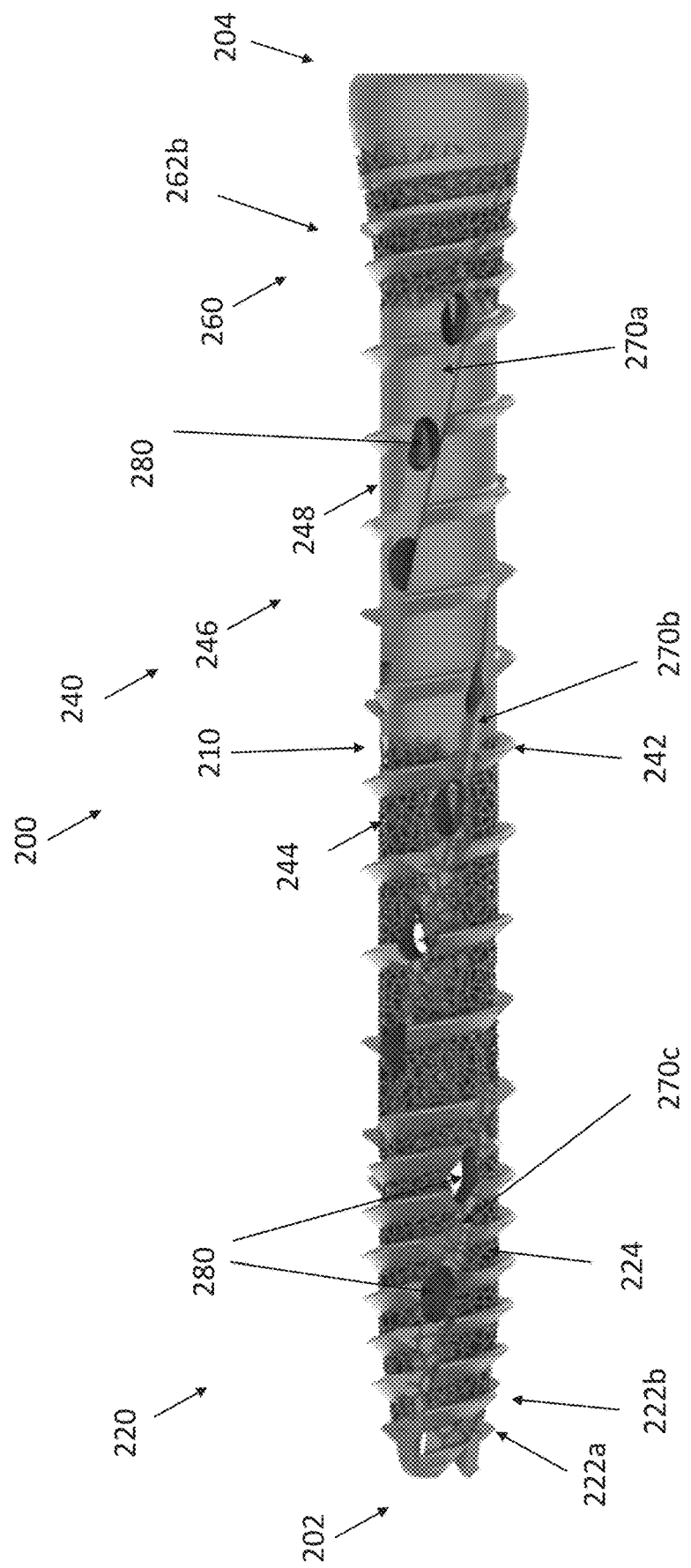
FIG. 2 is a side view of an exemplary threaded implant.

FIG. 2 illustrates an exemplary threaded bone implant 200. Implant 200 may have one or more features of implant 100 in FIG. 1, including features that may be similarly labeled (e.g., 120 and 220). One difference between implant 100 and implant 200 is that implant 200 includes a central region, a proximal portion 246 of which is void or free of a porous network of interconnected struts. Proximal portion 246, which may be considered a solid portion, is disposed at the SI joint when the implant is fully implanted. The proximal portion 246 of the central single threaded region 240 includes inner member or inner shank 248 and a thread radially extending therefrom. In some embodiments, implant 200 may be the same as implant 100 in all other ways. As shown in FIG. 2, shank 248 in proximal portion 246 has the same or substantially the same radial dimension (e.g., diameter) as the porous network of interconnected struts 244 in the distal portion of the central region 240. An exemplary advantage of the proximal portion 246 without the lattice, and the larger diameter shank in proximal portion 246, is that proximal region 246 may be stronger and more fatigue resistant in the region of the larger diameter shank. This may be important on some bone implants with certain dimensions where including a lattice structure along its entire length, including a region across the SI joint, may reduce fatigue strength to an extent that is undesired. For example, in some embodiments, implant 200 may have a major diameter from 9 mm to 11 mm (outer diameter of the thread), such as 10 mm.

As shown in FIG. 2, inner shank 248 has step-up in region 210 in central region 240, where the diameter of the shank increases at the step-up from the distal portion of central region 240 to proximal portion 246 of central region 240. The step-up in shank diameter increases the fatigue strength in the proximal portion 246, which is generally positioned across the joint.

FIGS. 3-6 illustrate exemplary lag threaded implants 300-600, respectively, in which the central regions and proximal regions are not threaded, as shown. The lag implants include a proximal washer, as shown, methods of use of which are generally known for lag implants. In some applications, the threaded lag implants herein may be used for fracture and repair, for example.

Figure 3:
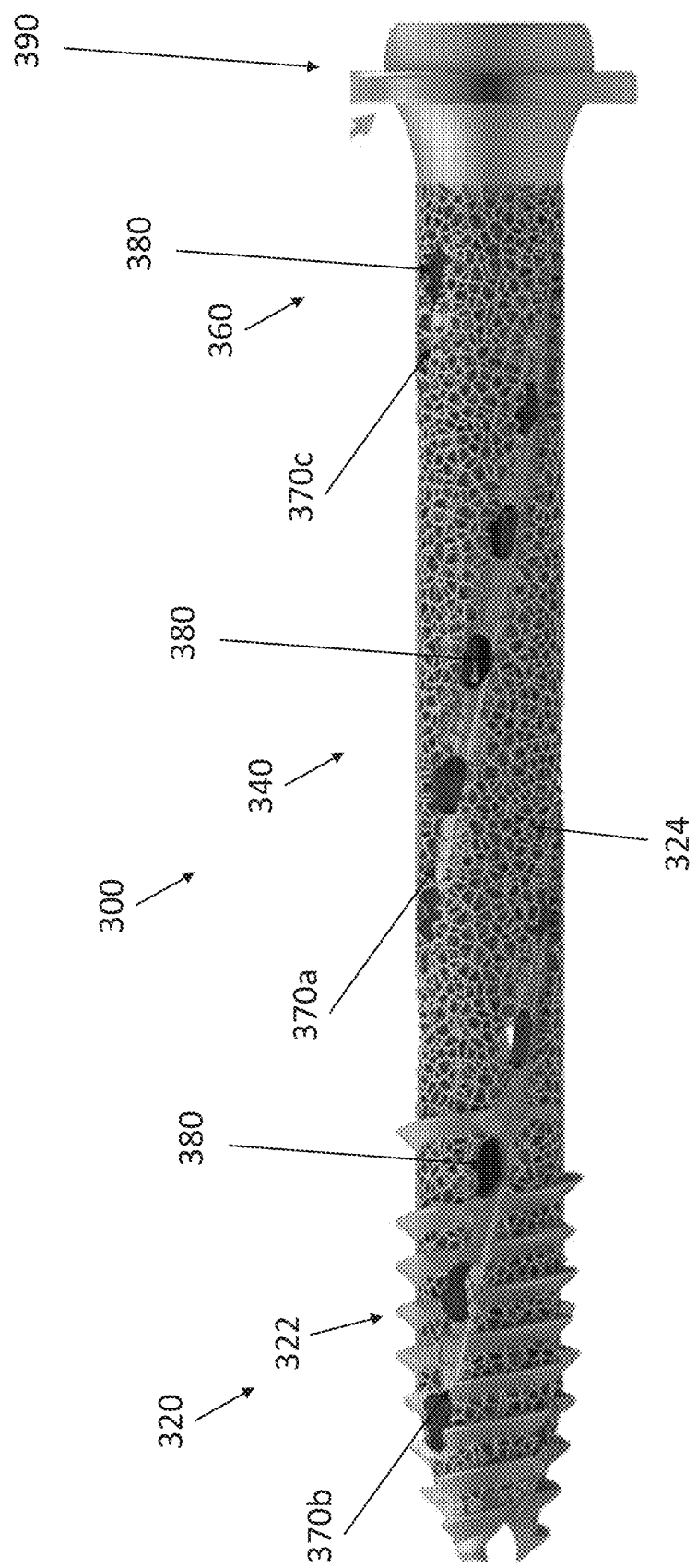
FIG. 3 is a side view of an exemplary threaded implant.

FIG. 3 illustrates an exemplary threaded lag implant 300 that includes a distal threaded region 320, a central non-threaded region 340 spaced to be disposed across a SI joint, and a proximal non-threaded region 360. Distal region 340 is multi-lead, and in this embodiment in dual-lead. Implant 300 includes a plurality of helical flutes or fluted region 370 (e.g., 370a, 370b and 370c, as shown). Implant 300 further includes a plurality of fenestrations 380, which may be similar or the same as any of the fenestrations herein. For example, and as shown, each of the helical flutes 370 is aligned with a plurality of fenestrations 380. Fenestrations in the distal region 320 may be larger than fenestrations in the central and/or proximal regions 340 and 360 respectively, such as for the reasons set forth herein.

As shown in FIG. 3, implant 300 includes porous lattice or network of interconnected struts 324, additional exemplary details of which are described herein. Porous lattice 324 may also be considered to have a helical configuration, disposed between both threads 322 and the flutes, as shown. In this example, the porous lattice extends in the distal region 320, the central region 340, and into the proximal region 360. Any of the description herein related to a porous network of interconnected struts may be incorporated into lattice 324. Washer 390 is also shown, and is configured to be disposed about the proximal end of implant 300 and allows for a range of motion between implant 300 and washer 390.

Figure 4:
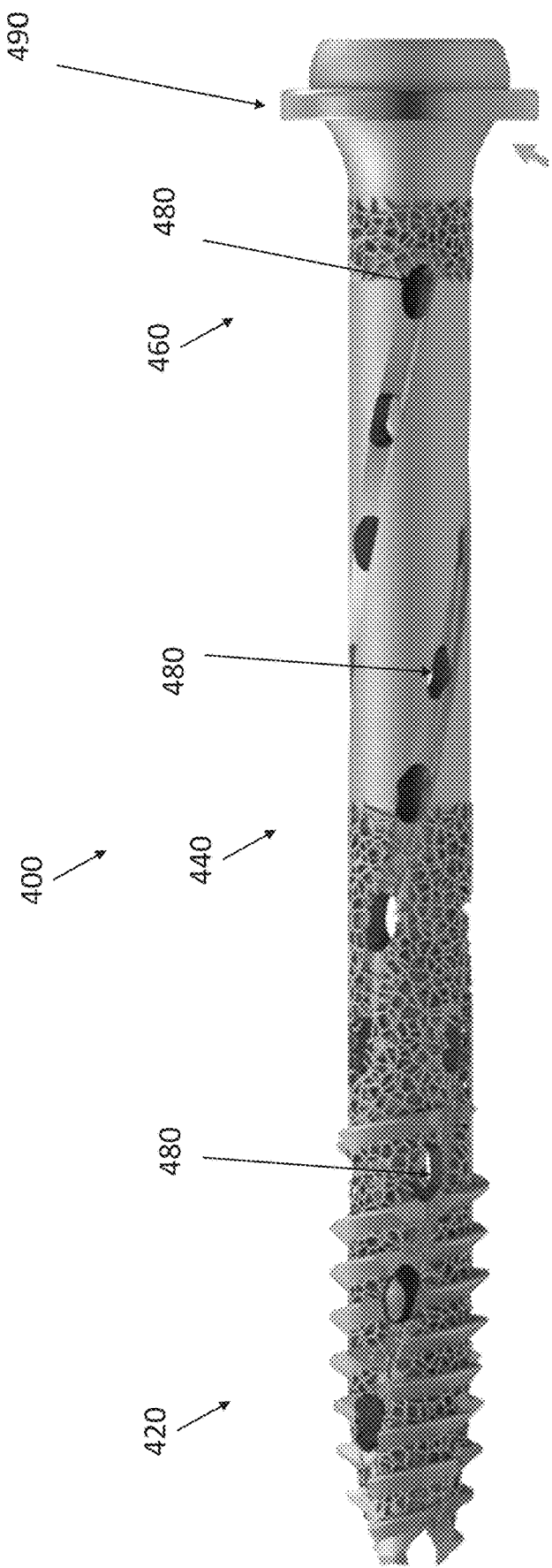
FIG. 4 is a side view of an exemplary threaded implant.

FIG. 4 illustrates implant 400 and illustrates features similar or the same as implant 200 in FIG. 2, in particular a proximal portion of central region 440 that is free of a porous lattice. The relevant description of FIG. 2 with respect to a section free of a porous lattice is incorporated by reference into the description of implant 400 in FIG. 4 for all purposes. An exemplary advantage of the proximal portion of the central region 440 without the lattice as shown, and the larger diameter shank in the proximal portion of central region 440, is that the proximal region may be stronger and more fatigue resistant in the region of the larger diameter shank, for the same reasons set forth herein with respect to FIG. 2.

Figure 5:
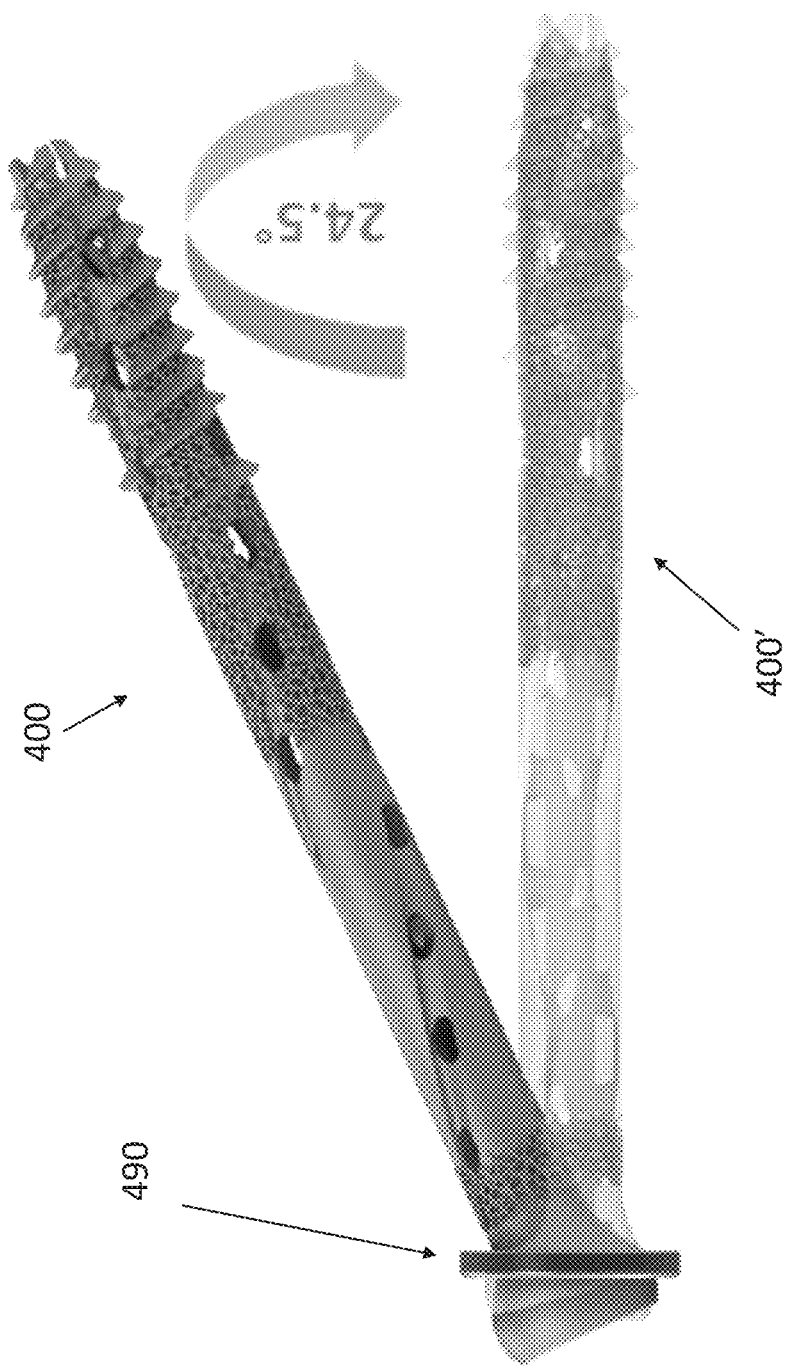
FIG. 5 is a side view of an exemplary lag threaded implant and washer.

FIG. 5 illustrates implant 400 from FIG. 4, and also illustrates an exemplary angle of rotation and washer 490, with implant 400' shown to illustrate the exemplary angle of rotation.

Figure 6:
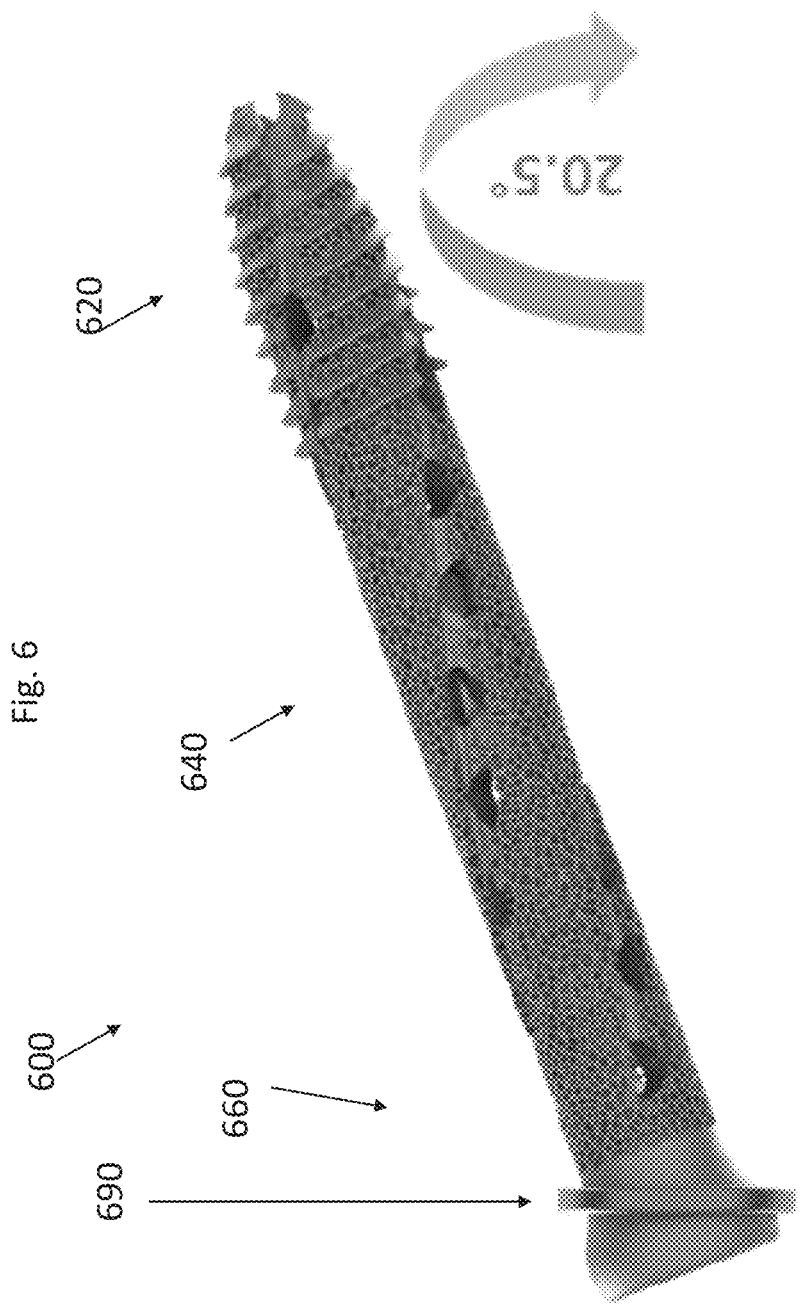
FIG. 6 is a side view of an exemplary lag threaded implant and washer.

FIG. 6 illustrates implant 600 that may be similar or the same as implant 300 shown in FIG. 3. FIG. 6 illustrates an exemplary angle of rotation and 690. Any suitable description herein related to implant 300 is incorporated by reference into the disclosure of FIG. 6.

Figure 7:
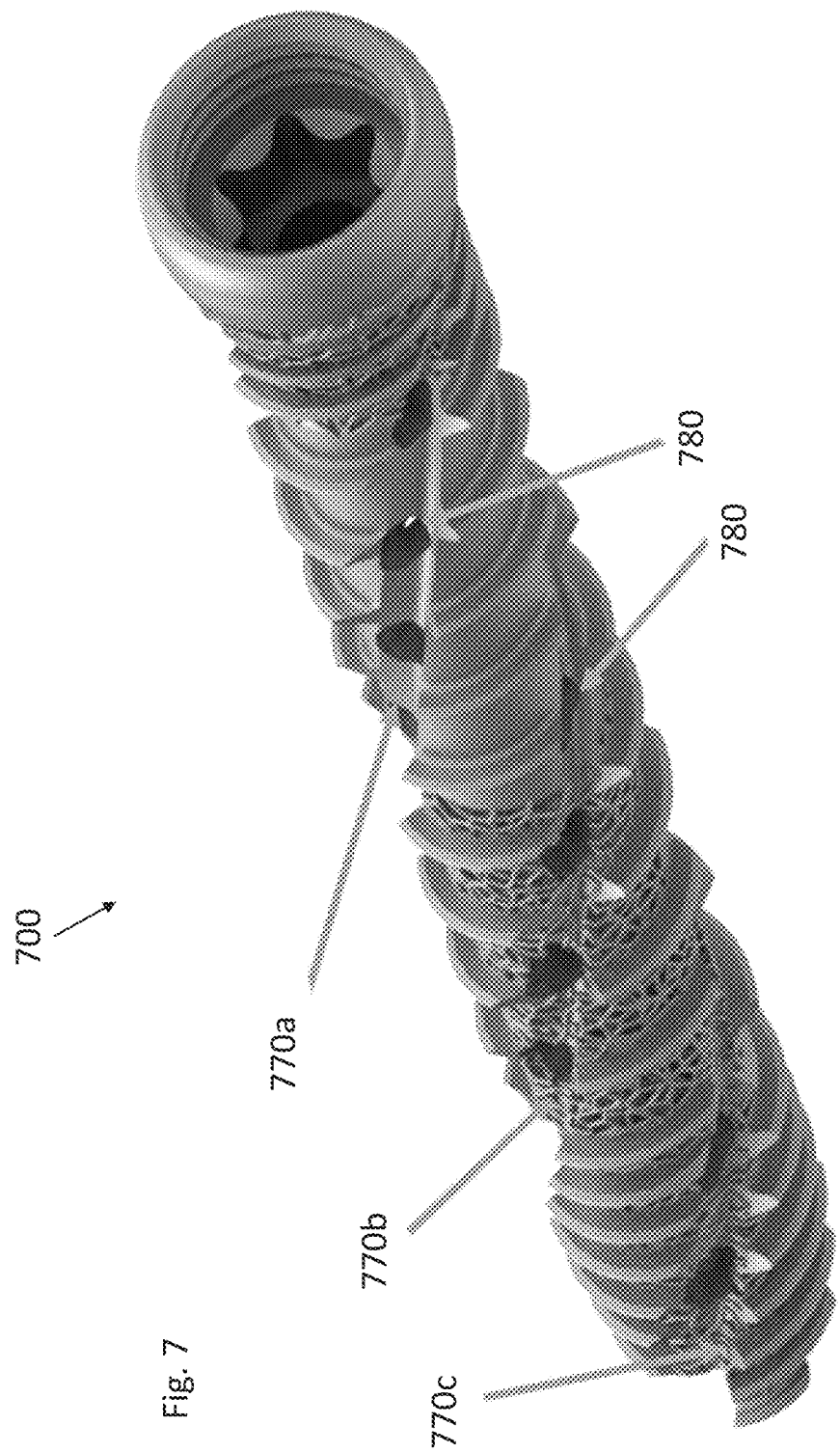
FIG. 7 is a perspective view of an exemplary threaded implant.

Threaded bone implants herein may include one or more flutes, or fluted regions, examples of which are shown in FIGS. 1-6. FIG. 7 illustrates exemplary threaded bone implant 700, which may include any other suitable feature of any other threaded bone implant described herein. Implant 700 has an elongate body that includes a plurality of helical flutes or fluted regions 770a, 770b, 770c, extending along at least a portion of the length of the elongate body. Similarly, FIG. 2 shows implant 200 including a plurality of helical flutes 270a, 270b and 270c formed therein. Threaded bone implants herein may include three flutes (as shown in the examples of FIGS. 2 and 7), although implants herein may be modified to include more or fewer than three flutes.

Implant 700 also includes fenestrations 780, only two of which are labeled in FIG. 7. Implant 700 is another example of an implant body that includes flutes 770 that are each aligned with a separate plurality of fenestrations 780 formed through the elongate body. Each fluted region in this example includes a separate plurality or set of fenestrations aligned with the respective fluted region, as is shown in FIG. 7.

FIGS. 2 and 7 show exemplary implants that include a plurality of helical flutes, each of which extends from the distal region and into and through the central region, and which may optionally extend in the proximal regions. As shown in FIG. 2, the plurality of helical flutes may extend to a minimal extent into the proximal multi-lead region 260, but the flutes may optionally not extend all the way through proximal regions herein.

As is shown in FIGS. 2 and 7 (but shown in other embodiments herein), the flutes or fluted regions (as well as one or more of the fenestrations) of the implant create an interruption in the one or more threads that extend around the elongate body.

The threaded implants herein may include one or more fenestrations, or relatively larger apertures, extending therethrough. FIG. 2 illustrates a plurality of fenestrations 280 (only two of which are labeled). FIGS. 2 and 7 are examples of threaded implants in which at least one (optionally all) of the fenestrations is aligned, or overlaps with, a fluted region of the implant. FIGS. 2 and 7 each illustrate a plurality of fluted regions of the respective threaded implant, each of which is aligned or overlapped with a plurality of fenestrations. The fenestrations aligned with or overlapping each of the fluted regions are axially spaced apart along the fluted region, and together the fenestrations are disposed in a helical configuration, as shown more clearly in FIG. 7. In FIGS. 2 and 7, for example, there are three sets of helically-oriented fenestrations, each set including a plurality of fenestrations.

Figure 8:
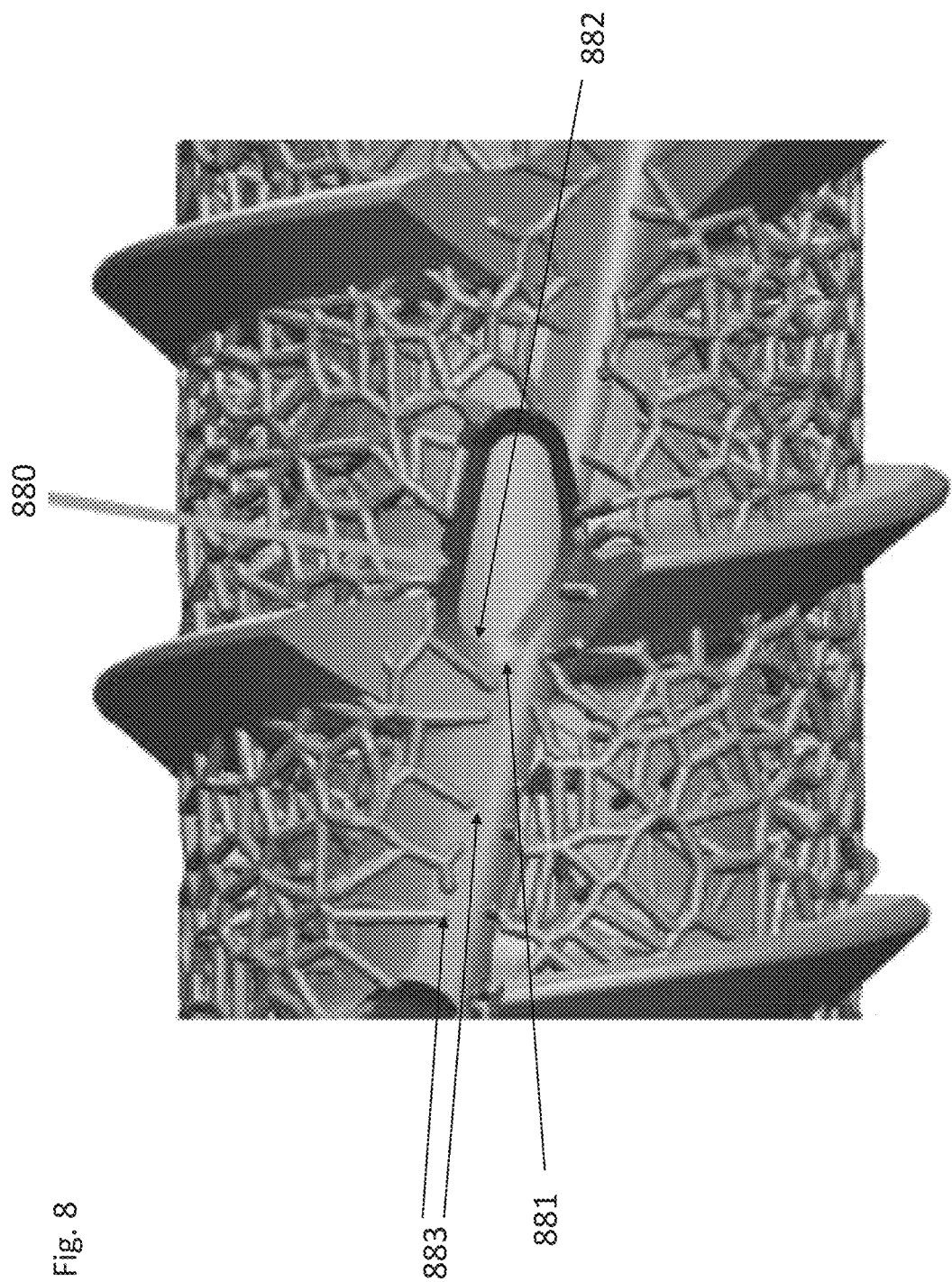
FIG. 8 is a side view of an exemplary threaded implant including a fluted region, a fenestration, and a porous network of interconnected struts.

In any of the embodiments herein, any or all of the fenestrations in the implant may have a tapered configuration in the radial direction. FIG. 8 illustrates a single fenestration 880 in a threaded implant elongate body having a tapered configuration between a larger radially outer fenestration opening 881 and a smaller radially inner fenestration opening 882, wherein the difference in opening sizes defines the tapered configuration. This type of taper is referred to herein as a radially inward taper. Any or all of the fenestrations in the threaded implant may be tapered in this manner. Fenestration 880 is also an example of a fenestration aligned with a fluted region, as shown. FIG. 8 is also an example of a continuous thread, as shown, that is interrupted by a fluted region and fenestration 880.

Any of the implants herein may have a plurality of fenestrations, but not all of the implant fenestrations may have the same size or configuration as one or more other fenestrations in the implant. For example, in some embodiments, a distal region of the implant (e.g., distal region 220 in FIG. 2) may not need to have as much fatigue strength as a more proximally disposed region, such as central region 240, or a proximal portion 246 of the central region, which may be implanted across a SI joint. Any of the implants herein may thus have distal regions with one or more fenestrations therein that are larger than one or more fenestrations in at least a portion of the central region that is disposed across the SI joint. The threaded implant central regions may have smaller fenestration so that the implant has more structural material in the region that is disposed across the SI joint. The distal region, which may not need the same fatigue strength, can have more openings, such as in the form of larger fenestrations, without negatively impacting strength of the implant.

Additionally, any of the implants herein may include fenestrations in the distal region that have less pronounced tapers in which there is less of a difference in size or circumferential area between the radially inner opening and the radially outer opening (i.e., a steeper transition between the inner opening and the outer opening). Compared to one or more central region fenestrations, distal region fenestrations may have radially inner openings that are relatively larger than radially inner openings in the central region of the implant.

As described herein, any of the implants herein may include porous regions disposed radially outward from an inner member or shank, wherein the porous regions extend along at least a portion of the threaded implant, including in regions in between the one or more threads. For example, FIG. 1 shows implant 100 that includes porous network of interconnected struts (e.g., 124) in between threads and extending along substantially all of the elongate body. FIG. 2 shows an example of an implant 200 that includes porous regions (e.g., 224) in between threads and extending along at least a distal region of an implant, and in a proximal region of the implant.

Figure 9:
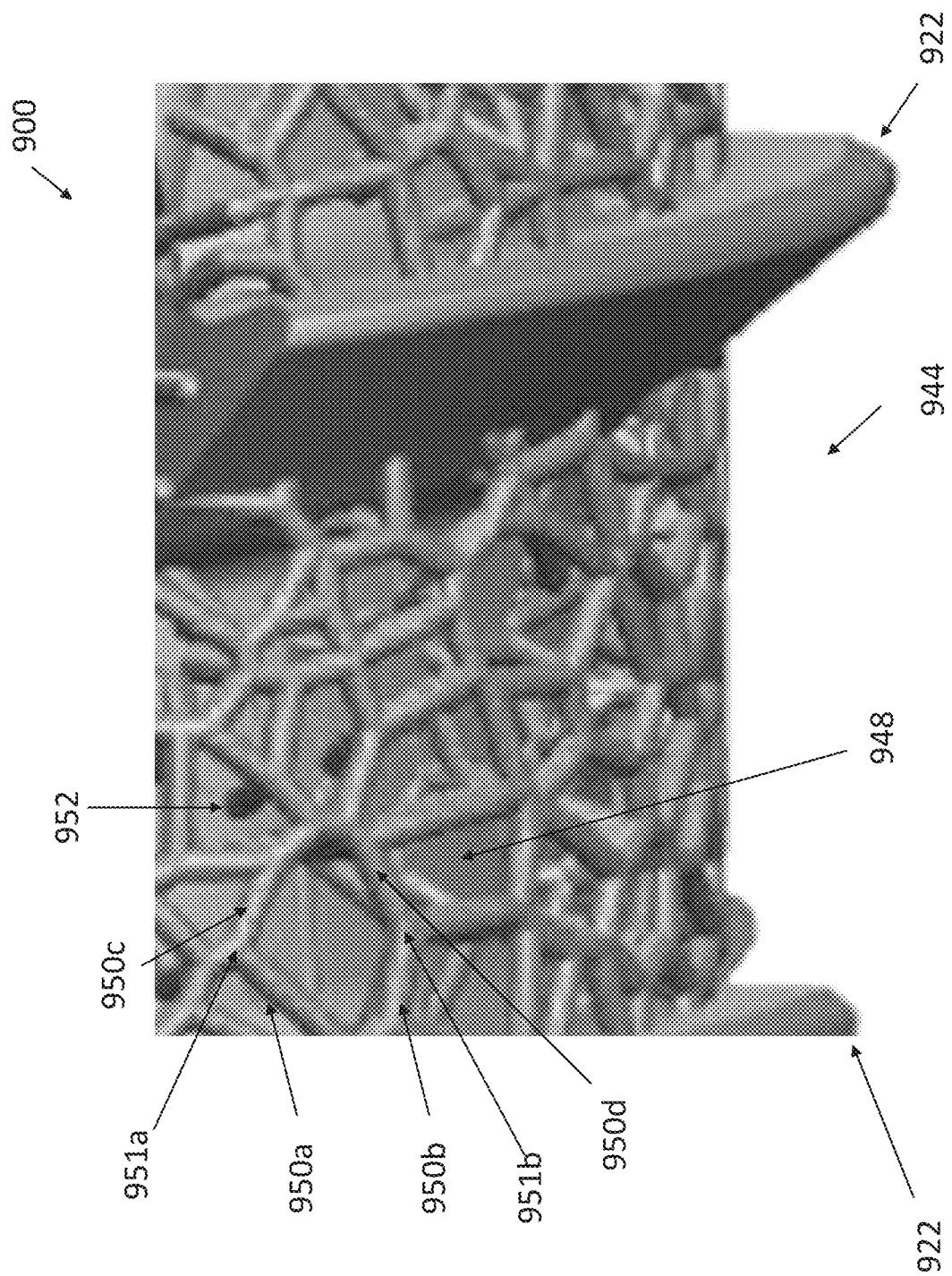
FIG. 9 is a side view of an exemplary threaded implant including a porous network of interconnected struts between threads.
Figure 10:
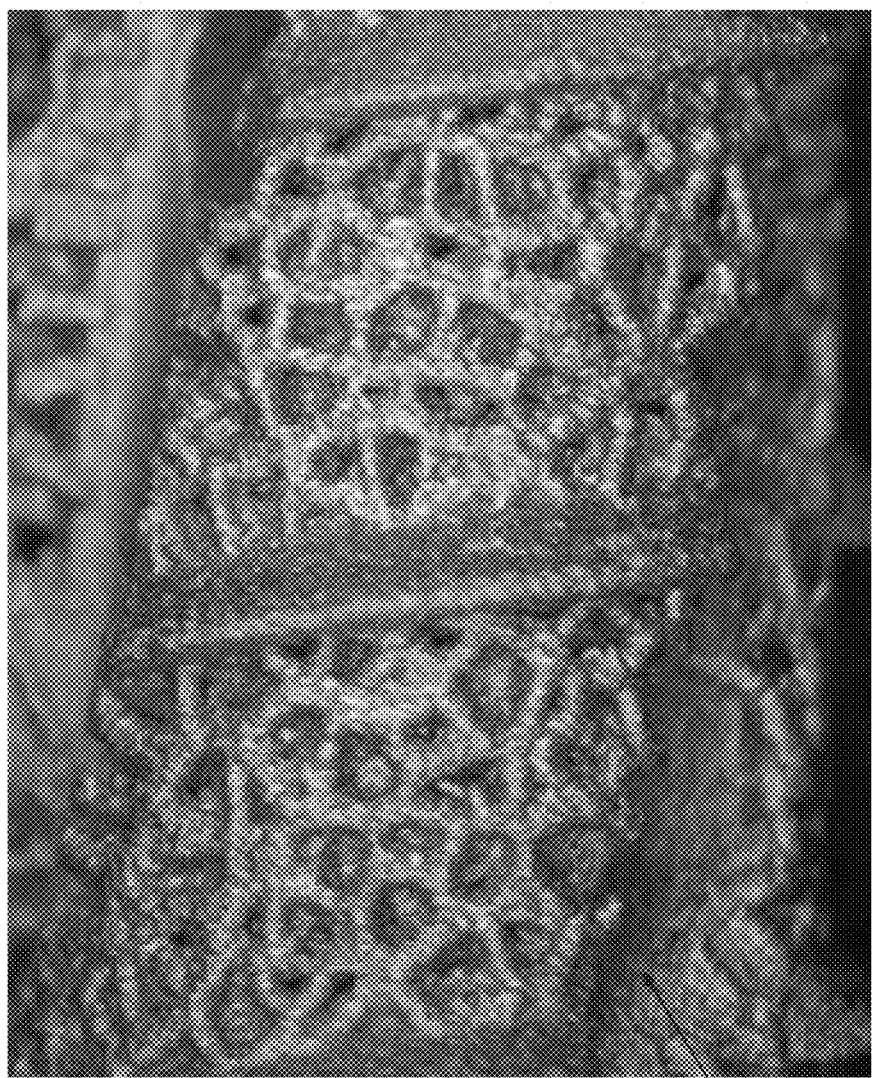
FIG. 10 is a side view of an exemplary threaded implant including flutes, as well as a porous network of interconnected struts disposed between threads.

Any of the porous network of interconnected struts herein (e.g., lattice 144 in FIG. 1, porous lattice 244 in FIG. 2) may be a porous network of interconnected struts disposed about the inner shank, an example of which is shown in FIG. 9.

With threaded implants such as those described herein, it may be desirable to have the porous network of interconnected struts that are between the threads to rotationally approximate a smooth shank and thereby facilitate a smooth rotational entry into the bone. This can create a minimal amount of resistance and bony damage as the threaded implant is rotated through bone, helping securely anchor the threaded implant into bone. This may be contrasted with porous region that include struts with many free ends that extend radially outward and are not interconnected with other struts as a network. The porous regions herein may be configured as a porous network of interconnected struts that are disposed about an inner shank (e.g., 948), an exemplary highlighted region of which is shown in FIG. 9.

FIG. 9 illustrates a portion of an exemplary implant 900 including thread 922, in between which the implant includes a porous network of interconnected struts 944. Network of interconnected struts 944 includes a plurality of interconnected struts 950 (e.g., 950a, 950b, 950c), only some of which are labeled in FIG. 9 for clarity. The struts 950 are interconnected at connections or nodal locations 951, and only two of which are labeled for clarity—951a and 951b. The connections or nodal locations herein may be the connection of two, three, four, or more individual struts or beams of the porous network of interconnected struts. As set forth above, the porous network of interconnected struts preferably creates a smooth outer surface and may approximate a cylindrical shank (even though the network defines a plurality of pores between the struts), which facilitate a relatively smooth rotation of the implant through bone.

The porous network of interconnected struts has an outer dimension less than a major diameter (diameter of thread(s)) of the at least one helical thread, which is shown in at least FIGS. 8 and 9.

The porous networks of interconnected struts herein may be defined in a variety of ways. For example, the porous network of interconnected struts may be considered to be substantially concentric about a long axis of the elongate body in at least a portion of the porous network of interconnected struts, which is partially shown in the perspective view of FIG. 7. Additionally, the interconnected struts in the porous networks of interconnected struts herein may be considered to have the same radially outermost dimension and concentric about an elongate body long axis. The porous networks of interconnected struts herein may be considered to define a generally circular shape in an end view of the elongate body, which is partially shown in FIG. 7. Additionally, the interconnected struts in the porous networks of interconnected struts herein may be considered to approximate an outer cylindrical profile, even though there are pores defined by the struts, and even though threads may interrupt sections of the outer cylindrical profile. Additionally, the porous network of interconnected struts may be considered to define a generally cylindrical outer profile, even though there are pores defined by the struts, and even though threads may interrupt sections of the generally cylindrical profile. Additionally, the porous networks of interconnected struts may be considered to define a substantially smooth outer surface, even though there are pores defined by the struts. Additionally, any of the porous networks of interconnected struts herein may be considered to include radially outer struts, which are substantially free of strut free ends extending radially outward.

As shown in FIG. 9, the porous lattice may further include a plurality of generally radially extending struts 952 that extend radially outward from the inner shank or inner member 948 and connect to the porous network of interconnected struts. The plurality of radially extending struts 952 generally couple the inner shank 948 to the outer porous network of interconnected struts. Radially extending struts as described in this context (e.g., strut 952) are not necessarily orthogonal, as they may have some radial dimension in addition to some axial dimension.

In any of the embodiments herein, the porous network of interconnected struts includes struts or beams, any of which may have a diameter from 0.175 mm to 0.300 mm.

In any of the embodiments herein, the porous network of interconnected struts may include point spacings from 0.375 mm to 0.525 mm.

In some embodiments herein, such as is shown in FIG. 1, the porous networks of interconnected struts may have or define a general helical configuration extending along the elongate body between the at least one helical thread. Helically extending porous networks herein may have interruptions formed therein and are still considered to have helical configurations.

Any of the porous networks of interconnected struts herein may include one or more end regions including strut free ends (e.g., 883 in FIG. 8), wherein the strut free ends are coupled or extending from a fluted region of the elongate bone implant body, particularly in embodiments in which the threaded implanted is 3D printed. A strut free end in this context refers to a strut end that is not directly connected to another strut, and may be directly connected to another portion of the implant such as an inner shank, a thread or a flute, for example.

Figure 11:
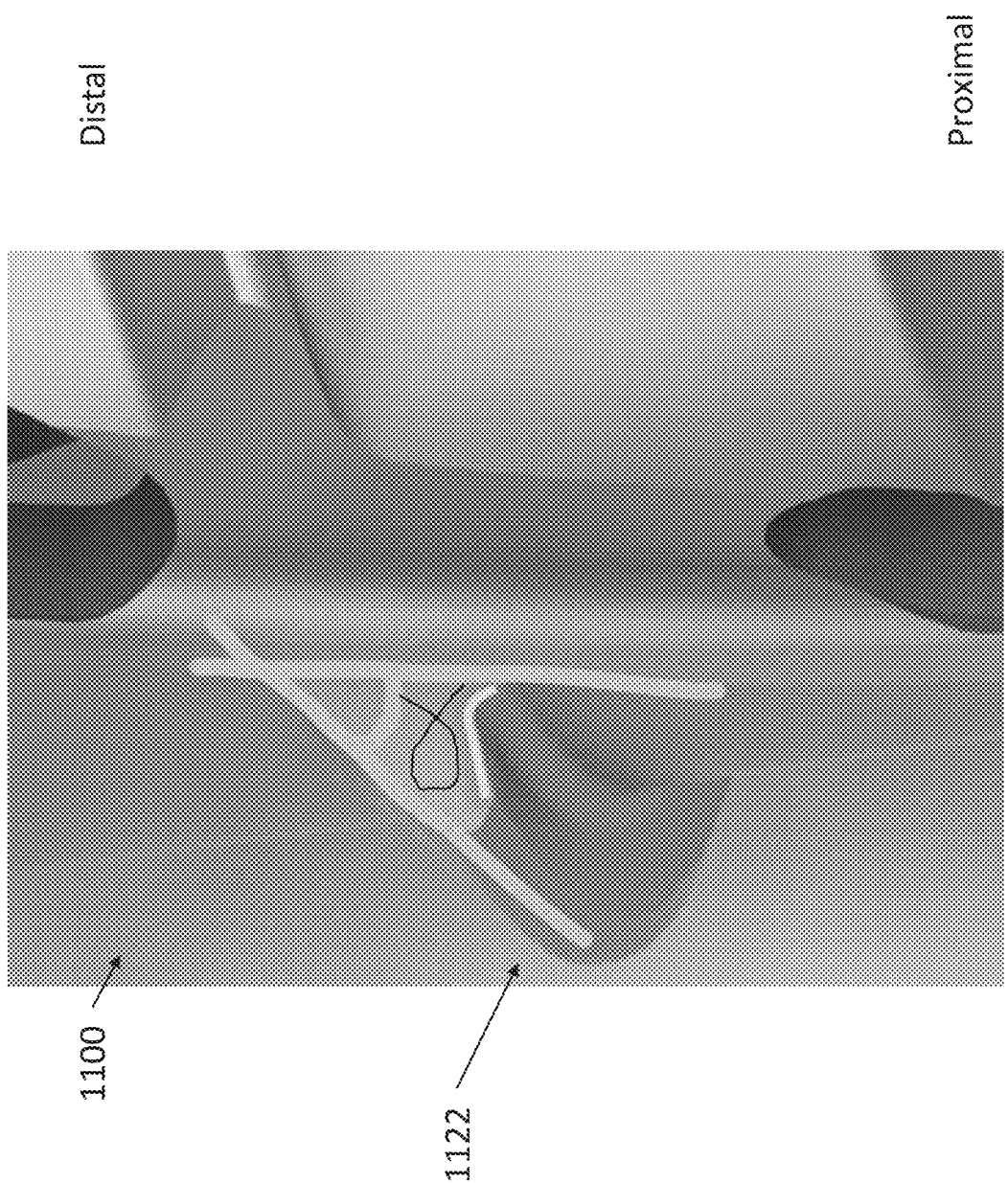
FIG. 11 illustrates an exemplary thread angle alpha referenced herein.

Any the threaded implants herein may be 3D printed, using one or more generally known methods or techniques. FIG. 11 illustrates a portion of an exemplary implant 1100, which may include any of the features of any of the threaded bone implants herein. Relative distal and proximal directions are labeled. Thread 1122 shown in FIG. 11 may be the same or substantially the same as any of the threads shown in the examples of FIGS. 1-10. When threaded bone implants herein, including the threads described herein, are 3D printed with the proximal or head side down, the threads are printed in the orientation shown in FIG. 11. When angle alpha as shown is large enough, the threads may tend to droop proximally (towards the head) during a 3D printing process. For example, in some embodiments, alpha may be greater than 45 degrees, such as from 45 degrees to 75 degrees, such as 45 degrees to 65 degrees. 3D printing some types of threaded bone implants in a head-to-tip direction may thus produce threads that do not have the desired configuration after the printing process.

Figure 12B:
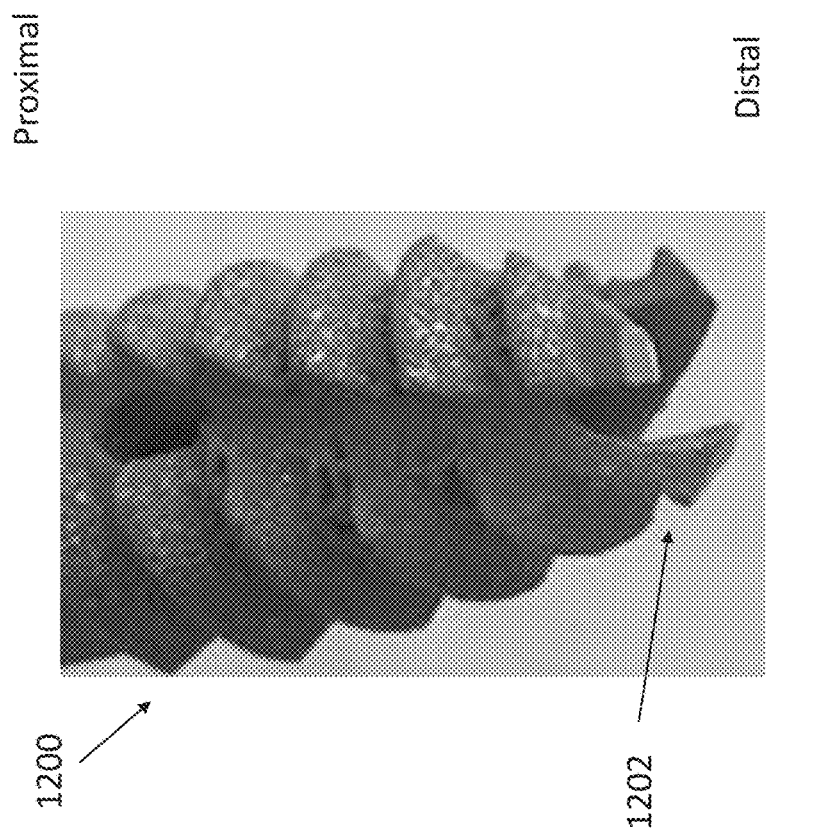
FIGS. 12A and 12B illustrates an exemplary orientation for manufacturing threaded implants herein.
Figure 12A:
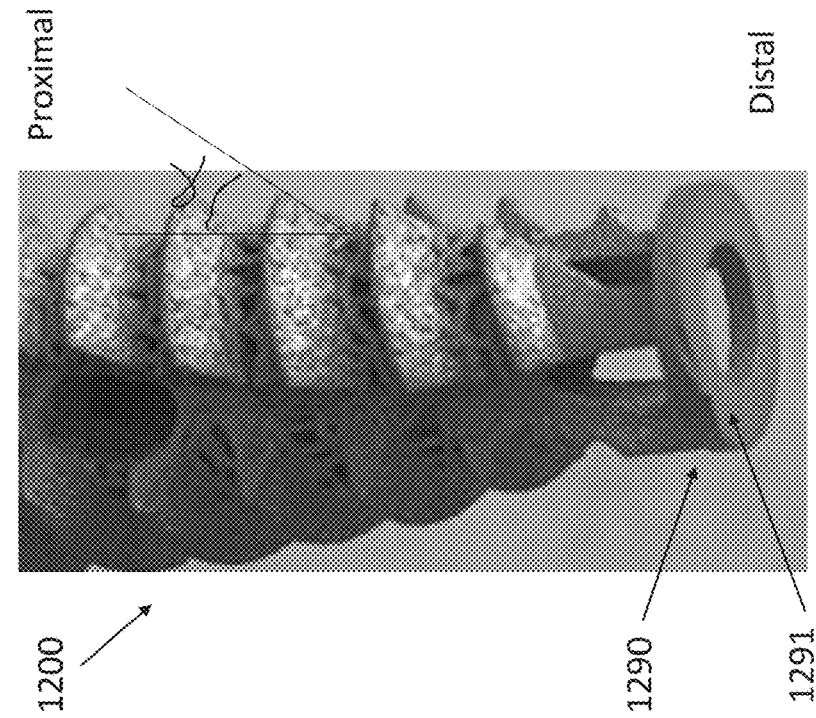

One option to manufacture threaded bone implants with threads that are disposed at certain angles is to print the threaded implants from the tip end (distal end) up to the head end (proximal end), the orientation of which is generally shown in FIG. 12A. Printing in this orientation may, depending on the thread angles, produce threads at angles that are beneficially less likely to droop or sag during the printing process. To print some threaded bone implants, it may be important to have a sturdy base upon which to print the implant upward to maintain a vertical long axis throughout the printing process. FIG. 12A illustrates an exemplary distal portion of 3D printed threaded implant 1200, including a printed sacrificial tip 1290 with a flattened base 1291, which is removed (e.g., machining away) after the printing process to create the finished and optionally sharpened distal tip configuration shown in FIG. 12B. In this example, the sacrificial tip 1290 includes a flattened base 1291 that provides a sturdy base upon which the implant may be printed up towards the head or proximal region. Printing in this orientation with an optional sacrificial sturdy base may allow for 3D printing some threaded implants that would be challenging to print if attempts were made to print from the proximal head upward to a distal tip end.

One aspect of the disclosure is a method of a method of 3D printing a threaded bone implant (such as any of the threaded implants herein). The method may include printing a threaded bone implant from a distal end to a proximal end. The method may include printing an inner shank, printing at least one helical thread extending along at least a portion of the threaded bone implant and extending from the inner shank. The method may also include printing a porous network of interconnected struts about the inner shank, about a long axis of the elongate bone implant body, and between at least a section of the at least one helical thread, where the porous network of interconnected struts has an outer dimension less than a major diameter of the at least one helical thread. The method may include printing the porous network of interconnected struts to be substantially concentric about a long axis of the elongate body in at least a portion of the porous network of interconnected struts. The method may include printing the porous network of interconnected struts to have a general helical configuration extending along the elongate body between the at least one helical thread and about the inner shank. The method may include printing the porous network of interconnected struts to have the same radially outermost dimension and concentric about an elongate body long axis. The method may include printing strut ends that are disposed within and coupled to fluted regions of the implant. The method may include printing the porous network of interconnected struts to define a substantially smooth radially outer surface that approximate a cylindrical profile.

One aspect of the disclosure is a method of printing a threaded bone implant. The method may include 3D printing a sacrificial distal tip and printing a threaded bone implant above the sacrificial tip. The method may include removing the sacrificial tip (e.g., machining it away) and forming a distal end, optionally sharpened, on the distal end of the bone implant after removing the sacrificial tip.

It is understood that features of one or more embodiments herein may be integrated with one or more other embodiments herein unless the disclosure indicates to the contrary.

What is claimed is:

1. A threaded bone stabilization implant adapted and sized for placement across a sacro-iliac ("SI") joint, comprising:
an elongate body having a distal end and a proximal end;
the elongate body including a threaded distal region, a threaded central region disposed proximally of the distal region, and a proximal region disposed proximally of the central region,
the elongate body further including a plurality of helical flutes, each of the plurality of helical flutes having formed therethrough a plurality of fenestrations extending into a central lumen,
the elongate body having a length, and the threaded distal region, the threaded central region, and the proximal region each having individual lengths such that when the implant is laterally implanted, the threaded distal region is positioned in a sacrum, the threaded central region is positioned across an SI-joint, and the proximal region is positioned in an ilium,
wherein each of the plurality of helical flutes has formed therethrough a first set of one or more fenestrations extending into the central lumen in the threaded distal region and a second set of one or more fenestrations extending into the central lumen in the threaded central region, at least one of the one or more fenestrations in the distal region is larger than at least one of the one or more fenestrations in the central region.

2. The implant of claim 1, wherein the threaded distal region is a multi-lead distal region, the threaded central region is a single-lead central region, and the proximal region is a multi-lead proximal region.

3. The implant of claim 1, further comprising, an inner shank from which one or more threads extend radially, and a porous network of interconnected struts disposed about the inner shank.

4. The implant of claim 1, wherein the plurality of helical flutes consists of three helical flutes.

5. The implant of claim 1, wherein each of the plurality of fenestrations has a radially inward taper.

6. The implant of claim 1, wherein the length of the distal region is from 10 mm to 22 mm, the length of the central region is from 8 mm to 56 mm, and the length of the proximal region is from 6 mm to 10 mm.

7. A threaded bone stabilization implant adapted for placement across a sacro-iliac ("SI") joint, comprising:
   an elongate body having a distal end and a proximal end;
   the elongate body including a threaded multi-lead distal region, a threaded single-lead central region disposed proximally of the multi-lead distal region, and a threaded multi-lead proximal region disposed proximally of the single-lead central region;
   the body having a length, and the threaded multi-lead distal region, the threaded single-lead central region, and the threaded multi-lead proximal region each having individual lengths such that when the implant is laterally implanted across an SI joint, the multi-threaded lead distal region is positioned in a sacrum, the single-lead central region is positioned across the SI-joint, and the multi-lead proximal region is positioned in an ilium,
   wherein the elongate body further comprises a plurality of helical flutes formed therein, each of the plurality of helical flutes extending in the multi-lead distal region, the single-lead central region, and optionally into the multi-lead proximal region,
   wherein each of the plurality of flutes has a plurality of fenestrations aligned with the respective flute, the plurality of fenestrations spaced from each other along a length of the flute and extending into an elongate body central lumen, and
   wherein each of the plurality of fenestrations has a radially inward taper.

8. The implant of claim 7, wherein one or more fenestrations of the plurality of fenestrations in the distal region has a greater angle tapered configuration than one or more fenestrations of the plurality of fenestrations in the central region.

9. The implant of claim 7, wherein the multi-lead distal region is a dual-lead region and the multi-lead proximal region is a dual-lead region.

10. The implant of claim 7, wherein the multi-lead distal region, the single-lead central region, and the multi-lead proximal region each comprise an inner shank from which the respective threads extend, the implant further comprising a porous network of interconnected struts disposed about the inner shank.

11. The implant of claim 7, wherein the plurality of helical flutes consists of three helical flutes.

12. The implant of claim 7, wherein a length of the distal region is from 10 mm to 22 mm, a length of the central region is from 8 mm to 56 mm, and a length of the proximal region is from 6 mm to 10 mm.

\* \* \* \* \*